US012752077B2

(12) United States Patent
Fantuzzi et al.

(10) Patent No.: US 12,752,077 B2
(45) Date of Patent: Oct. 6, 2026

(54) EXPANDABLE SHEATH WITH FOLD

(71) Applicant: ABIOMED, Inc., Danvers, MA (US)

(72) Inventors: Glen R. Fantuzzi, Danvers, MA (US); Robert Fishman, Danvers, MA (US); Jonathan Barry, Danvers, MA (US); Anne Gabrielle McLoughlin, Danvers, MA (US)

(73) Assignee: ABIOMED, Inc., Danvers, MA (US)

( * ) Notice: Subject to any disclaimer, the term of this patent is extended or adjusted under 35 U.S.C. 154(b) by 694 days.

(21) Appl. No.: 18/201,462

(22) Filed: May 24, 2023

(65) Prior Publication Data

US 2023/0381455 A1 Nov. 30, 2023

Related U.S. Application Data

(60) Provisional application No. 63/346,226, filed on May 26, 2022.

(51) Int. Cl.
*A61M 25/00* (2006.01)
*A61M 25/01* (2006.01)
(Continued)

(52) U.S. Cl.
CPC .... *A61M 25/0023* (2013.01); *A61M 25/0012* (2013.01); *A61M 25/01* (2013.01);
(Continued)

(58) Field of Classification Search
CPC ...... A61M 25/0662; A61M 2025/0024; A61M 25/0023; A61M 25/005;
(Continued)

(56) References Cited

U.S. PATENT DOCUMENTS 4,634,432 A * 1/1987 Kocak ............... A61M 39/0606 604/167.04
5,484,425 A * 1/1996 Fischell .............. A61M 25/005 604/528
(Continued)

FOREIGN PATENT DOCUMENTS

CN 206372159 U * 8/2017 ........ A61M 25/0662
EP 2995268 A1 3/2016
(Continued)

OTHER PUBLICATIONS

International Search Report and Written Opinion for corresponding Application No. PCT/US2023/023366 dated Oct. 19, 2023 (15 pages).

*Primary Examiner* — Wesley G Harris
(74) *Attorney, Agent, or Firm* — BOTOS CHURCHILL IP LAW LLP

(57) ABSTRACT

The systems, methods, and devices that provide an expandable sheath assembly for insertion of an interventional medical device (e.g., an intracardiac heart pump) into a blood vessel through a vessel aperture. The assembly may have an elongate sheath body having a proximal end, a distal end, and a lumen extending from the proximal end to the distal end. The sheath body may have a first layer, wherein the first layer is a liner defining the lumen. The sheath body may have a second layer disposed over the first layer, wherein the second layer is a patterned structure. The sheath body may have a third layer disposed over the second layer. The elongate sheath body may include a slit through the second layer and the third layer, wherein the slit extends along at least a portion of the elongate sheath body. A first portion of the elongate sheath body may overlap a second portion of the elongate sheath body along the slit to form a fold.

22 Claims, 13 Drawing Sheets

B - B

(51) Int. Cl.

| | |
|---|---|
| ***A61M 60/13*** | (2021.01) |
| ***A61M 60/216*** | (2021.01) |
| ***A61M 60/865*** | (2021.01) |

(52) U.S. Cl.
CPC .......... *A61M 60/13* (2021.01); *A61M 60/216* (2021.01); *A61M 60/865* (2021.01); *A61M 2025/0024* (2013.01); *A61M 25/0045* (2013.01); *A61M 2025/0047* (2013.01); *A61M 2025/0048* (2013.01)

(58) Field of Classification Search
CPC ...... A61M 2025/0681; A61M 25/0045; A61M 25/0668; A61M 60/865; A61M 2025/0025; A61M 2025/0675; A61M 25/0012; A61M 25/01; A61M 60/13; A61M 60/216; A61M 2025/0047; A61M 2025/0048; A61B 17/3439
See application file for complete search history.

(56) References Cited

U.S. PATENT DOCUMENTS

| | | | | |
|---|---|---|---|---|
| 5,533,986 | A * | 7/1996 | Mottola | A61M 25/0075 604/264 |
| 10,967,152 | B2 | 4/2021 | Korkuch | |
| 11,197,690 | B2 | 12/2021 | Fantuzzi et al. | |
| 2010/0198160 | A1 | 8/2010 | Voss | |
| 2013/0090624 | A1 * | 4/2013 | Munsinger | A61F 2/962 604/103.05 |
| 2014/0121629 | A1 * | 5/2014 | Macaulay | A61M 25/005 604/524 |
| 2014/0236123 | A1 * | 8/2014 | Birmingham | A61M 25/0012 604/524 |
| 2014/0275795 | A1 * | 9/2014 | Little | A61B 17/3423 600/208 |
| 2016/0213882 | A1 * | 7/2016 | Fitterer | B29C 53/08 |
| 2016/0296332 | A1 * | 10/2016 | Zhou | A61M 25/0662 |
| 2018/0256859 | A1 | 9/2018 | Korkuch | |
| 2019/0076167 | A1 | 3/2019 | Fantuzzi et al. | |
| 2021/0146111 | A1 | 5/2021 | Modlish et al. | |

FOREIGN PATENT DOCUMENTS

| | | | | |
|---|---|---|---|---|
| WO | WO-2007004531 | A1 * | 1/2007 | A61B 17/3439 |
| WO | WO-2008002915 | A2 * | 1/2008 | A61B 17/3439 |
| WO | WO-2018165519 | A1 * | 9/2018 | A61M 25/0023 |
| WO | WO-2021173750 | A1 * | 9/2021 | A61F 2/2436 |
| WO | 2022026026 | A1 | 2/2022 | |

* cited by examiner

EXPANDABLE SHEATH WITH FOLD

CROSS REFERENCE TO RELATED APPLICATION

This application claims the priority of and benefit from U.S. Provisional Application No. 63/346,226, filed May 26, 2022, which is incorporated by reference herein.

BACKGROUND

Interventional medical devices, such as, intracardiac heart pump assemblies may be introduced into the heart either surgically or percutaneously and used to deliver blood from one location in the heart or circulatory system to another location in the heart or circulatory system. For example, when deployed in the heart, an intracardiac pump may pump blood from the left ventricle of the heart into the aorta, or pump blood from the inferior vena cava into the pulmonary artery. Intracardiac pumps may be powered by a motor located outside of the patient's body (and accompanying drive cable) or by an onboard motor located inside the patient's body. Some intracardiac blood pump systems may operate in parallel with the native heart to supplement cardiac output and partially or fully unload the demands placed upon the heart. Examples of such systems include the IMPELLA® family of devices (Abiomed, Inc., Danvers Mass.).

In one approach, an intracardiac blood pump is inserted by a catheterization procedure through the femoral artery using a sheath, such as a peel away introducer sheath. The sheath may alternatively be inserted in other locations such as in the femoral vein or any path for delivery of a pump for supporting either the left or right side of the heart.

The introducer sheath may be inserted into the femoral artery through an arteriotomy to create an insertion path for the pump assembly. A portion of the pump assembly is then advanced through an inner lumen of the introducer sheath and into the artery. The requisite size of the arteriotomy is a matter of intense interest. Accordingly, expandable introducer sheaths have been developed so that a smaller arteriotomy opening is required to accommodate the sheath and the medical device passed therethrough. Accordingly, improvements in expandable introducer sheaths continue to be sought.

BRIEF SUMMARY

The systems, methods, and devices described herein provide an expandable sheath assembly for insertion of an interventional medical device (e.g., an intracardiac heart pump) into a blood vessel through a vessel aperture. The expandable sheath assembly includes a sheath body having multiple layers. The layers of the sheath body include a liner defining a lumen extending from the proximal end to the distal end of the sheath body, a patterned structure disposed over the liner, and a jacket or cover disposed over the patterned structure. The sheath body includes a slit through at least the patterned structure and cover. In some aspects, the liner is also slit. The slit extends from the distal end of the sheath body toward the proximal end of the sheath body. The sheath body is arranged such that a first portion of the sheath body along the slit overlaps a second portion of the sheath body along the slit to form a fold. In some aspects, a seal is disposed over the cover to seal the slit of the sheath body. The arrangement of the sheath body of the present technology enables the sheath body to momentarily expand radially during passage of an interventional device through the lumen of the sheath in response to the radial tension caused by the passage of the interventional device through the lumen. Upon removal of the interventional device from the lumen, the sheath body automatically relaxes (i.e., radially contracts) back to the original state (or a state that is substantially similar or proximate to the original state).

In one aspect of the present technology, an expandable sheath is provided comprising an elongate sheath body having a proximal end, a distal end, and a lumen extending from the proximal end to the distal end. The elongate sheath body comprises a first layer, a second layer, and a third layer. The first layer is a liner defining the lumen. The second layer is disposed over the first layer and the second layer is a patterned structure. The third layer disposed over the second layer. The elongate sheath body includes a slit through the second layer and the third layer, wherein the slit extends along at least a portion of the elongate sheath body. The first portion of the elongate sheath body overlaps a second portion of the elongate sheath body along the slit to form a fold.

In some aspects, the elongate sheath body is configured to radially expand from an unexpanded state to an expanded state to allow passage of a portion of a medical device through the lumen and the portion of the medical device has a transverse cross-sectional area larger than a transverse cross-sectional area of the lumen when the elongate sheath body is in the unexpanded state.

In some aspects, the medical device is an intracardiac heart pump.

In some aspects, when the elongate sheath body is radially expanded, the overlap between the first portion of the elongate sheath body and the second portion of the elongate sheath body is decreased and the transverse cross-sectional area of the lumen thereby increases.

In some aspects, the elongate sheath body is configured to relax when the portion of the medical device is removed from the lumen such that the transverse cross-sectional area of the lumen is decreased and the elongate sheath body substantially returns to the cross-sectional area in the unexpanded state.

In some aspects, the first layer is made of polytetrafluoroethylene (PTFE) or an elastomer.

In some aspects, the first layer includes a lubricious coating on an interior surface of the first layer.

In some aspects, the first layer includes a hydrophilic coating on an interior surface of the first layer.

In some aspects, the slit of the elongate sheath body is further through the first layer.

In some aspects, the first layer includes a folded portion that extends along at least a portion of the elongated sheath.

In some aspects, in a transverse cross-section of the first layer, the first layer is continuous and does not include any breaks in a circumference of the first layer.

In some aspects, the second layer is made of metal.

In some aspects, the metal is stainless steel or nitinol.

In some aspects, the patterned structure is a coil.

In some aspects, the patterned structure is embedded within the third layer.

In some aspects, the third layer is made of thermoplastic.

In some aspects, the third layer is made of thermoplastic polyurethane (TPU) or a polyether block amid.

In some aspects, the elongate sheath body is tubular.

In some aspects, the elongate sheath body further comprises a fourth layer disposed over the third layer, the fourth layer configured to seal the fold in the elongate sheath body.

In some aspects, the fourth layer is made of an elastomer.

In some aspects, the fourth layer is made of TPU or silicone.

In some aspects, the expandable sheath further comprises a hub, wherein the proximal end of the elongate sheath body is coupled to the hub.

DETAILED DESCRIPTION

Figure 1:
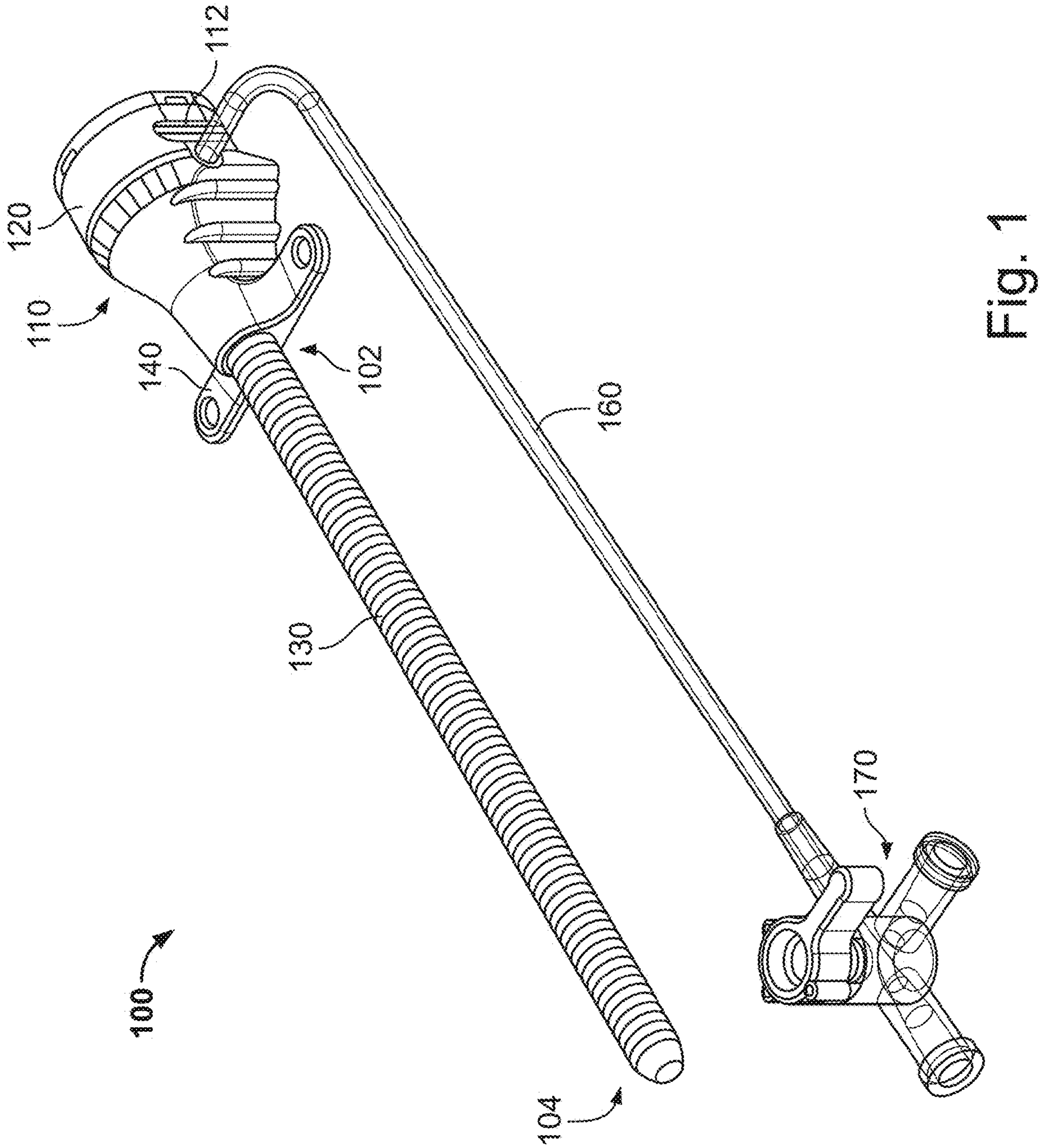
FIG. 1 illustrates a sheath assembly in accordance with an aspect of the present technology.

Aspects of the present disclosure are described in detail with reference to the figures wherein like reference numerals identify similar or identical elements. It is to be understood that the disclosed aspects are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

To provide an overall understanding of the systems, method, and devices described herein, certain illustrative aspects will be described. Although the apparatus and its features described herein are specifically described for use in connection with an intracardiac heart pump system, it will be understood that all the components and other features outlined below may be combined with one another in any suitable manner and may be adapted and applied to other types of medical devices such as electrophysiology study and catheter ablation devices, angioplasty and stenting devices, angiographic catheters, peripherally inserted central catheters, central venous catheters, midline catheters, peripheral catheters, inferior vena cava filters, abdominal aortic aneurysm therapy devices, thrombectomy devices, TAVR delivery systems, cardiac therapy and cardiac assist devices, including balloon pumps, cardiac assist devices implanted using a surgical incision, and any other venous or arterial based introduced catheters and devices.

As used herein, including in the claims, "tubular" does not necessarily mean having a circular cross section. A tubular item may, for example, have an oval, polygonal, irregular, or other shaped cross section.

Since commercially available tear away introducer sheaths are typically not radially expandable, the inner diameter of the introducer sheath must always be large enough to accommodate the largest diameter portion of the pump assembly, which is typically the pump head, even if other parts of the pump assembly, such as the catheter, have a significantly smaller diameter. In this example, the introducer sheath creates an opening that has an outer diameter wider than necessary to allow passage of the pump catheter into the vessel. Then, the introducer sheath is peeled or torn away and replaced with a lower-profile repositioning sheath. Removing the introducer sheath by peeling it away presents several challenges. For example, introducers can tear too easily and/or prematurely, leading to bleeding or vascular complications. Some introducers may require excessive force to be peeled away for removal. If a physician applies too much force, when the introducer finally tears, the physician may inadvertently shift the position of the pump within the heart. The peel away introducer sheaths also complicate the design of the hemostatic valve located in the hub of the introducer which also needs to tear or otherwise separate. Further, a peel away introducer sheath leads to a larger vessel opening after the system is removed, which can complicate vessel closure.

Medical introducers, for applications other than inserting heart pumps, have expandable sheath bodies which may expand radially to allow passage of percutaneous devices into the patient's vasculature. These existing expandable introducers are for relatively short-term use and may be designed to prevent thrombosis between the sheath body and an indwelling catheter.

These introducers, when inserted, have an inner diameter smaller than the outer diameter of the device that will be introduced therethrough. The introducers are expandable to allow passage of the device through the sheath and into the vasculature. However, existing introducers have several shortcomings. For example, many currently available introducers require the user to interact with the sheath of the introducer to expand the introducer, e.g., by inflating or activating a component, which adds steps to the introduction process. Moreover, while these introducers may be expandable, the sheaths in these introducers do not decrease in size or contract after expansion or require manual intervention to bring about such decrease in size. Furthermore, the sheaths of these introducers include poor outer geometry smoothness. As a result, when these introducers are placed in the vasculature of the patient, thrombus formation or bleeding at the arteriotomy of the patient may occur over long-term use as rough outer edges of the sheath may lead to clot accumulation. Still further, some of these sheaths may lack structure that adequately resists kinking and buckling during typical anatomic bending conditions that occur during regular use of the introducers. In this regard, these sheaths may allow radial expansion, but do not allow for sheath compression/expansion in regions of the sheath not occupied by the device being passed therethrough, which may lower kink resistance. Moreover, these sheaths may have column strength issues and axial buckling of the sheath may be a problem, particularly during device removal. Finally, currently available introducer sheaths, as designed, may be unable to deliver large bore devices (i.e., devices that need to pass through a larger diameter sheath) without requiring unacceptable insertion and removal forces for advancing the devices through the sheath.

Thus, improvements in the design and performance of expandable introducer sheaths that may reduce or eliminate the deficiencies in current designs continue to be sought.

The systems, methods, and devices described herein provide an expandable sheath assembly for insertion of an interventional medical device (e.g., an intracardiac heart pump) into a blood vessel through a vessel aperture. The expandable sheath assembly includes a sheath body having multiple layers. The layers of the sheath body include a liner defining a lumen extending from the proximal end to the distal end of the sheath body, a patterned structure disposed over the liner, and a jacket or cover disposed over the patterned structure. The sheath body includes a slit through at least the patterned structure and cover. In some aspects, the liner is also slit. The slit extends from the distal end of the sheath body toward the proximal end of the sheath body. The sheath body is arranged such that a first portion of the sheath body along the slit overlaps a second portion of the sheath body along the slit to form a fold. A seal is disposed over the cover to seal the slit of the sheath body. The arrangement of the sheath body of the present technology enables the sheath body to momentarily expand radially during passage of an interventional device through the lumen of the sheath in response to the radial tension caused by the passage of the interventional device through the lumen. Upon removal of the interventional device from the lumen, the sheath body automatically relaxes (i.e., radially contracts) back to the original state (or a state that is substantially similar or proximate to the original state).

FIG. 1 shows a sheath assembly 100 in accordance with aspects of the present technology. The sheath assembly 100 has a hub 110, cap 120, sheath body 130, butterfly or suture pad 140, sidearm channel 160, and stopcock 170. The hub 110 works in concert with the cap 120 to secure the sheath body 130 in position. The hub 110 also has detents 112 (only one of which is visible in FIG. 1) to aid in attaching hub 110 to a dilator hub. The butterfly/suture pad 140 is configured to aid in attaching the sheath assembly 100 to the patient (e.g., by suturing the assembly to the patient). In the present description, the proximal end of the assembly100 is at the hub/cap end and the distal end of the assembly is at the tip end of sheath body 130. In this regard, sheath body 130 includes a proximal end 102 and a distal end 104. The proximal end 102 of the sheath body 130 is attached to the hub 110. Sheath body 130 includes a lumen, which extends from the proximal end 102 to the distal end 104. Sheath body 130 is configured to allow for passage of a medical device inserted therein via hub 110.

Fluid may be introduced into and/or withdrawn from the sheath assembly 100 via sidearm channel 160. Fluid flow through the device may be controlled by stopcock 170 (e.g., a 3-way stopcock). A hemostatic valve (not shown) may also be included within hub 110, the hemostatic valve being configured to prevent blood from leaking outside of the patient during insertion and/or removal of an intracardiac blood pump or other components. Although any suitable hemostatic valve may be employed, examples are described and illustrated in U.S. patent application Ser. No. 17/097,582 filed Nov. 13, 2020 and published as US 2021/0146111. In addition, in some implementations, the hub 110 may include a foam insert (not shown) placed proximal to the hemostatic valve that may be soaked with a lubricant such as silicone so that components will be lubricated as they are inserted through the foam and into the sheath body 130.

In one aspect, the lumen of sheath body 130 may have a fixed diameter. In this aspect, the diameter of the lumen should be large enough to accommodate the portion of the device inserted therethrough with the large diameter, even if other portions of the inserted device have significantly smaller diameters. For example, where the inserted device is an intracardiac heart pump, the portion of the device with the largest diameter may be the pump and/or motor assembly, whereas other portions, e.g., the catheter of the pump, may have significantly smaller diameters. Thus, in this case, the diameter of the lumen of sheath body 130 must be large enough to accommodate the pump assembly of the intracardiac blood pump. Usage of fixed diameter sheath bodies, such as sheath body 130, leads to large vessel openings after the system is removed, which can complicate vessel closure.

Alternatively, sheath assemblies with radially expandable sheath bodies may be provided in accordance with aspects of the present technology. Sheath assemblies with expandable sheaths are beneficial in the clinical setting to allow a physician to insert large interventional devices through a patient's vasculature without damaging the vessels. An expandable sheath body allows for use of a sheath body with a reduced diameter (i.e., smaller than the largest portion of the device to be inserted into the lumen of the sheath body) relative to fixed diameter sheath bodies, while still accommodating larger interventional devices by expanding during insertion. Expandable sheath bodies that have a small enough diameter may allow the practitioner to use commonly available medical instruments for closing the hole in the arteriotomy of the patient (that was made to allow insertion of the sheath assembly) after the sheath assembly is withdrawn from the patient. By allowing the use of such commonly available vessel closure devices, medical practitioners may use a wider range of medical instruments that is not limited to the class of instruments necessary for closing larger diameter holes in the arteriotomy of the patient. Moreover, by allowing for a smaller arteriotomy, expandable sheaths according to the present disclosure may aid in reducing bleeding or other complications that can arise in procedures requiring larger introducer sheaths.

Figure 2:
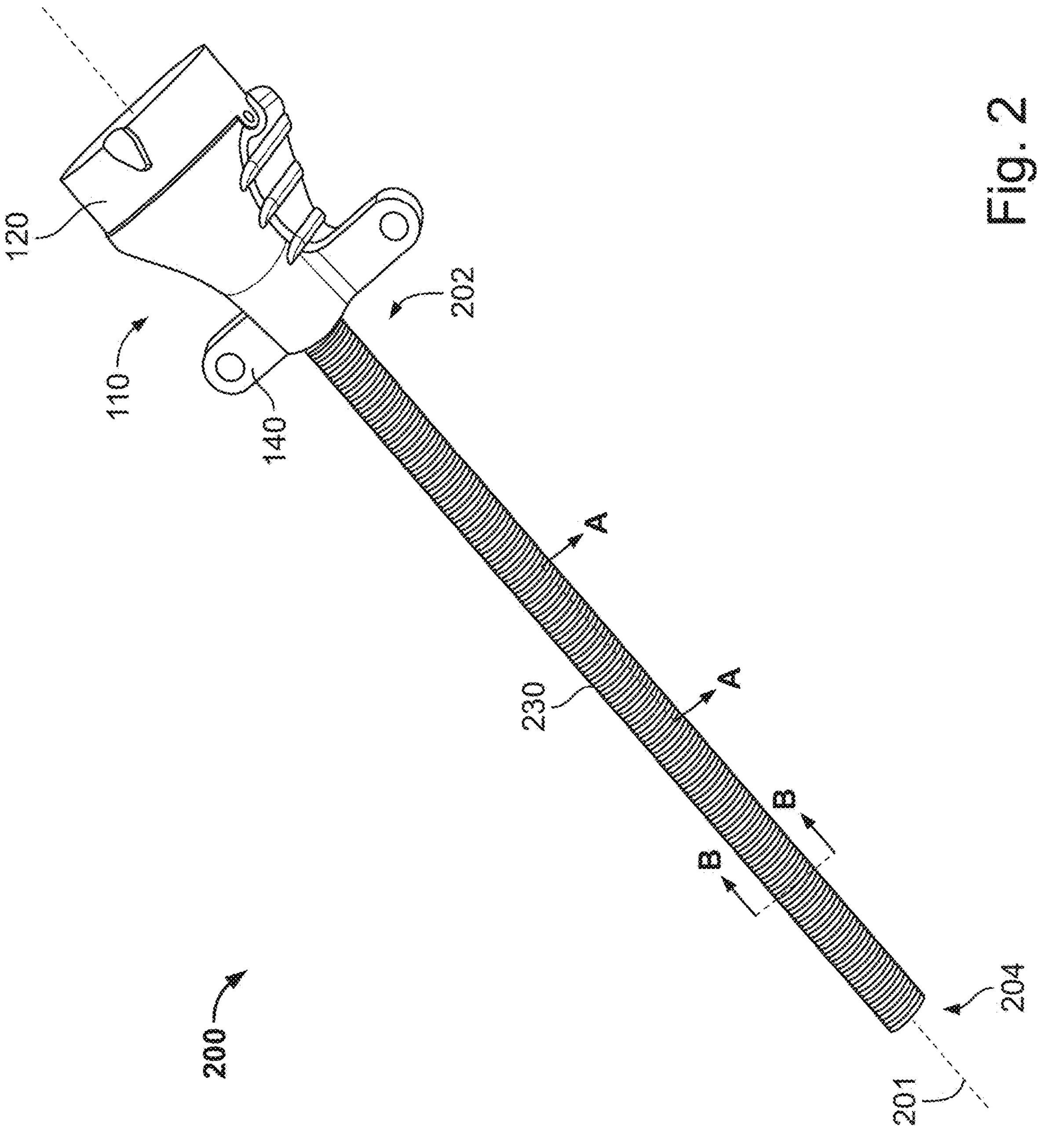
FIG. 2 illustrates a radially expandable sheath assembly in accordance with another aspect of the present technology.

Referring to FIG. 2, a sheath assembly 200 including a sheath body 230 that is radially expandable is shown attached to hub 110 in accordance with aspects of the present technology. Sheath body 230 has a proximal end 202, a distal end 204, and a lumen 232 (shown in FIGS. 3 and 4) extending from the proximal end 202 to the distal end 204. Sheath body 230 has an elongate, tubular shape and extends distally from hub 110 along longitudinal axis 201. Proximal end 202 is coupled to the hub 110. As will be described in greater detail below, sheath body 230 is multilayered and configured to radially expand from an unexpanded state to an expanded state to allow passage of interventional devices, such as an intracardiac blood pump, through the lumen 232 and then recoil to the unexpanded state after the interventional device has passed or been removed from the lumen 232.

Figure 3:
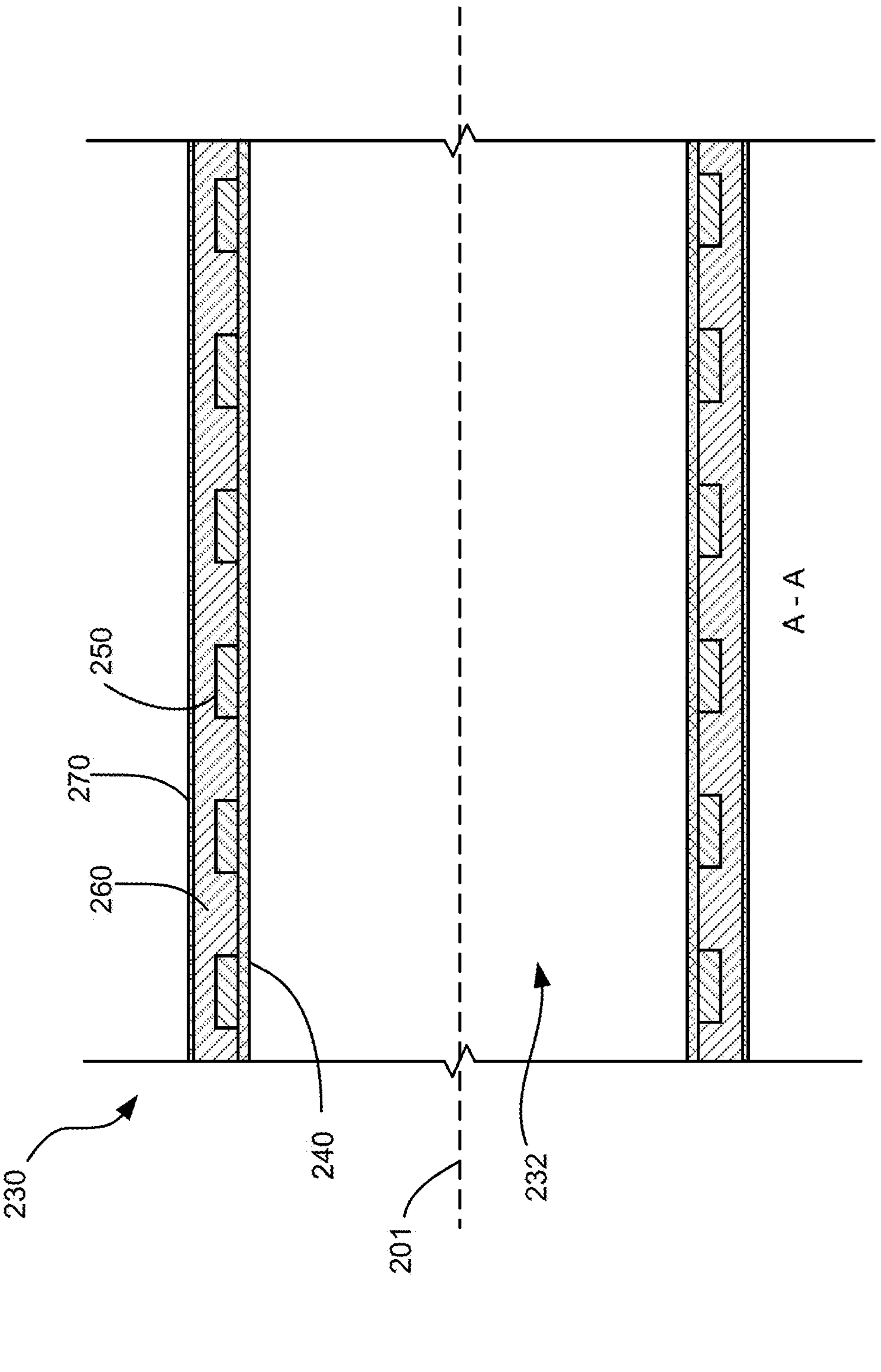
FIG. 3 is a longitudinal cross-sectional view of the sheath body of the sheath assembly of FIG. 2 along line A-A.
Figure 4:
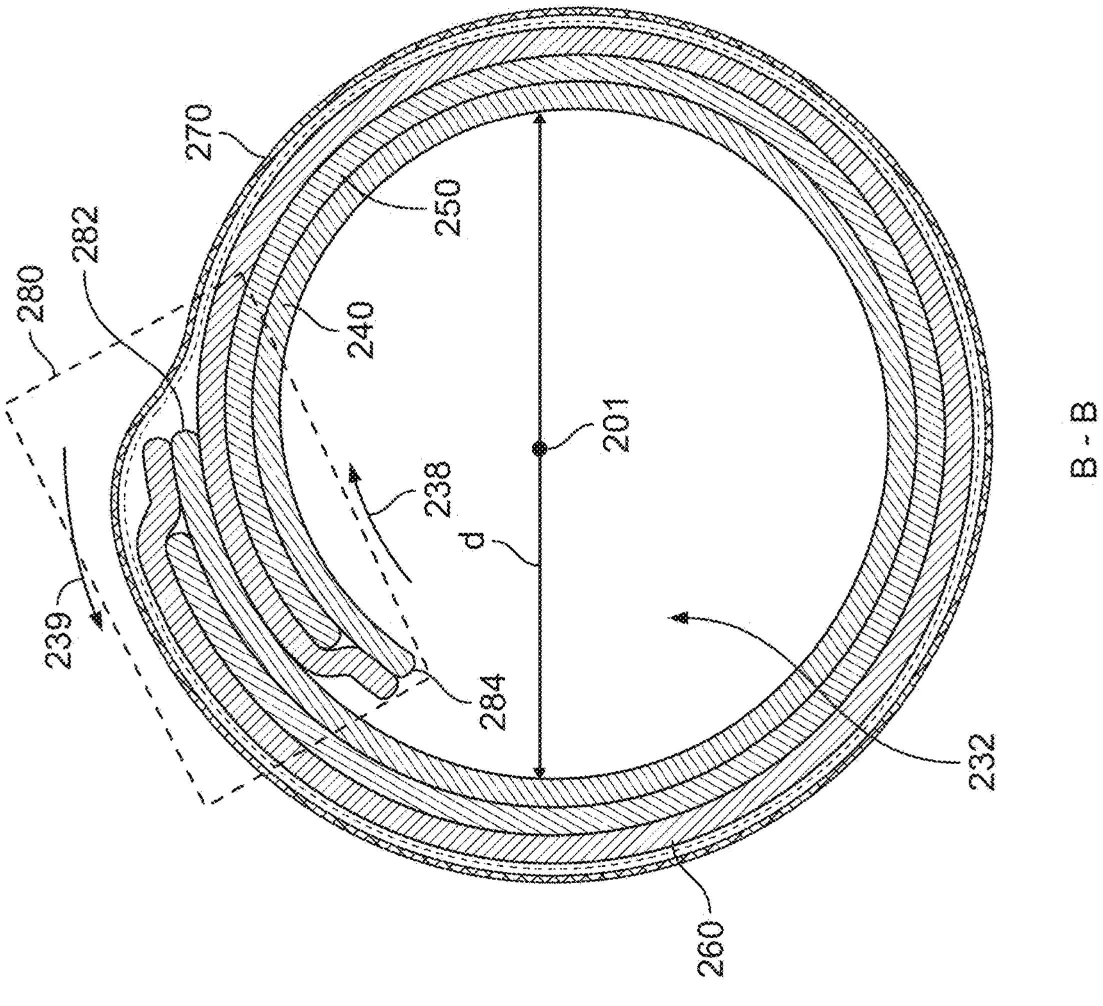
FIG. 4 is a transverse cross-sectional view of the sheath body of the sheath assembly of FIG. 2 along line B-B.

For example, referring to FIGS. 3 and 4, cross-sectional views of sheath body 230 are shown along lines A to A and B to B (shown in FIG. 2), respectively, in accordance with aspects of the present technology. The sheath body 230 comprises an inner liner 240 (first layer) defining lumen 232, a patterned structure 250 (second layer) disposed over the liner 240, and cover or jacket 260 (third layer) disposed over patterned structure 250 and liner 240. In one aspect, as shown in FIG. 3, the patterned structure 250 is embedded within cover 260 such that the inner surfaces of cover 260 and patterned structure 250 both contact the outer surface of liner 240. It is to be appreciated that liner 240, patterned structure 250, and cover 260 are coaxially arranged with respect to each other about longitudinal axis 201.

In one aspect, the liner 240 may have a smooth inner surface and be made of a polymer material, such as polytetrafluoroethylene (PTFE), fluorinated ethylene propylene (FEP), perfluoroalkoxy alkanes (PFA), ethylene tetrafluoroethylene (ETFE), etc., for lubricity and to facilitate insertion of interventional devices, such as, an intracardiac heart pump, through lumen 232 with minimal friction. In one aspect, the liner 240 may be made of an elastomer. In some aspects, the inner surface of liner 240 may have a lubricious coating such as a coating of hydrophilic material to further facilitate delivery of an interventional device through lumen 232.

In one aspect, patterned structure 250 is made of metal wire(s). The metal may be stainless steel or Nitinol. Alternatively, the patterned structure 250 may be made of other metals or rigid materials including non-metal materials. The patterned structure 250 may comprise wire(s) made of metal (or non-metal) that is coiled or arranged in other suitable wire patterns, such as, braids or weaves. The patterned structure 250 is configured to provide radial hoop strength to sheath body 230, which counteracts kinking during the bending of sheath body 230. The patterned structure 250 is also configured to provide structural rigidity to sheath body 230. Moreover, the patterned structure 250 has suitable elasticity and shape memory properties that enable sheath body 230 to momentarily radially expand during insertion of interventional devices and automatically radially contract upon their removal.

In one aspect, cover 260 is made of a polymer such as a thermoplastic polyurethane (TPU) or a polyether block amid, such as PEBAX, Vestamid, etc. It is to be appreciated that cover 260 may be made of a thermoplastic elastomer or other types of thermoplastics. Cover 260 is configured to encapsulate the patterned structure 250 and provide additional column strength and kink resistance for the sheath body 230. It is to be appreciated that cover 260 is made of a material that is more pliable than patterned structure 250. In one aspect, cover 260 has a shore hardness in the range of 30-72 D.

In one aspect, a jacket or seal 270 is disposed over cover 260 to seal sheath body 230. For example, seal 270 may be made of a low durometer (e.g., about 10 to about 80 durometer on the Shore A scale) elastomer, e.g., TPU, Silicone, etc. Seal 270 may be made of a TPU such as Carbothane PC3575 or silicone or silicone alternative such as Chronoprene T. As described below, it is to be appreciated that in other aspects, sheath body 230 is configured such that the sealing features of seal 270 may be provided by other components (e.g., liner 240) of sheath body 230 and seal 270 may be omitted from sheath body 230.

As best seen in FIGS. 4 and 5A-5C, in one aspect, sheath body 230 includes a longitudinal slit 234 through liner 240, patterned structure 250, and thermoplastic cover 260, where the slit 234 extends from distal end 204 toward proximal end 202. As described below, in another aspect, liner 240 is not slitted and the longitudinal slit 234 is included only through patterned structure 250 and cover 260.

As shown in FIG. 4, the slit 234 separates a first longitudinal edge 282 from a second longitudinal edge 284 of sheath body 230.

Figures 5A, 5B, 5C:
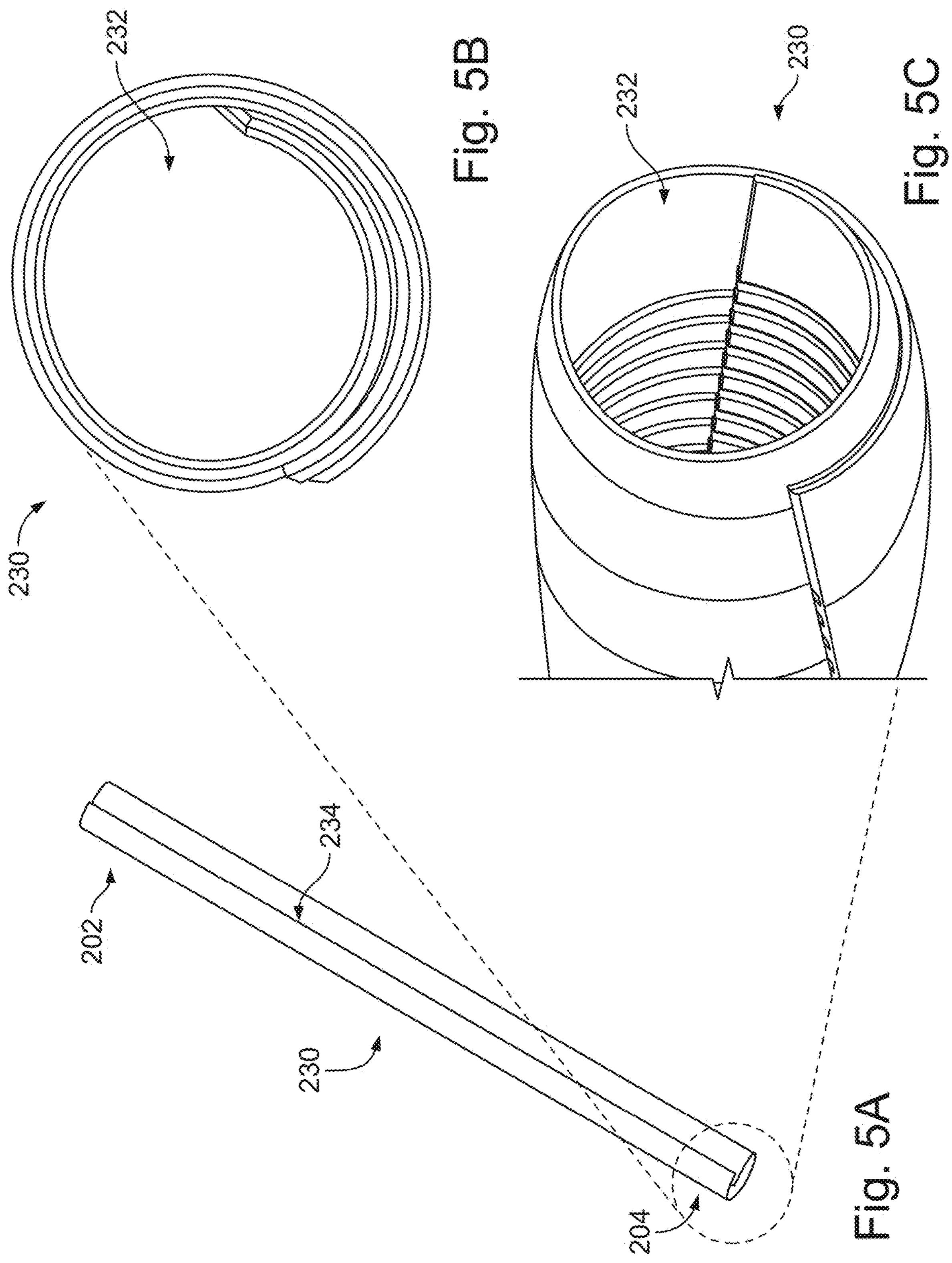
FIG. 5A is a perspective view of the sheath body of the sheath assembly of FIG. 2 in accordance with an aspect of the present technology.
FIGS. 5B and 5C are partial views of the distal end of the sheath body shown in FIG. 5A.

In one aspect, the slit 234 extends and terminates at proximal end 202, as shown in FIG. 5A. In another aspect, the slit 234 terminates a predetermined distance distal of proximal end 202. In the aspect where slit 234 terminates a predetermined distance distal of proximal end 202, there is a portion of sheath body 230 at the proximal end 202 that does not have a slit. This non-slitted proximal portion will not interact with the arteriotomy when the sheath body 230 is inserted into the patient and, therefore, does not need to collapse to a smaller diameter. The non-slitted proximal portion of sheath body 230 has a larger diameter than the slitted portion of sheath body 230. Moreover, the non-slitted proximal portion of sheath body 230 enables attachment to the hub and aids in hemostasis at the skin site of the patient.

In either case, sheath body 230 is coiled or overlapped with itself along the slit 234 such that the diameter of sheath body 230 is reduced (relative to a sheath body that is not overlapped and has a fixed diameter) and a first portion of sheath body 230 along slit 234 overlaps a second portion of sheath body 230 along slit 234 to form a longitudinal fold 280. In one aspect, a jacket or seal 270 is disposed over cover 260 to seal sheath body 230 and the slit 234 or fold 280. As noted above, seal 270 may be made of a low durometer (e.g., about 10 to about 80 durometer on the Shore A scale) elastomer, e.g., TPU, Silicone, etc., or other suitable materials. In one aspect, seal 270 is made of a shrink wrap or shrink film. As shown in FIGS. 3 and 4, the seal 270 is disposed over and encloses cover 260 and extends longitudinally from the proximal end 202 to the distal end 204. The seal 270 is configured to seal the slit 234 and prevent blood or other fluid from leaking out of lumen 232 through slit 234 or fold 280, e.g., when sheath body 230 is inserted into a patient.

In one aspect, the outer surface of seal 270 has a lubricious additive formed therein or thereon to reduce the overall coefficient of friction of sheath body 230 and aid in delivery of sheath body 230 into and through the vasculature of the patient. Moreover, the outer surfaces of seal 270 and cover 260 are both configured to be smooth to reduce thrombus formation or bleeding at the arteriotomy of the patient over long-term use of sheath body 230 in a patient. The smooth outer surfaces of seal 270 and cover 260 also reduce the insertion/removal forces required to insert and remove sheath body 230 into and out of the vasculature of the patient.

The slitted or coiled or overlapping arrangement of sheath body 230 enables sheath body 230 to be flexible and radially expandable about longitudinal axis 201 when a portion of an interventional device, such as an intracardiac blood pump, that is larger than the transverse cross-sectional area of lumen 232 when in an unexpanded state is introduced into the sheath body 210. For example, as shown in FIG. 4, before an interventional device is inserted into lumen 232, sheath body 230 is in an unexpanded or resting state. In the unexpanded state, lumen 232 has an inner diameter d and a first transverse cross-sectional area. After a portion of the interventional device that has a larger diameter than diameter d or a larger transverse cross-sectional area than the first transverse cross-sectional area of lumen 232 is inserted into lumen 232, the overlapping portions of sheath body 230 will move away from each other, as indicated by arrows 238, 239 in FIG. 4 and the amount of overlap will decrease. In this way, sheath body 230 momentarily radially expands to an expanded state to accommodate the larger dimensions of the inserted portion of the interventional device. In the expanded state, lumen 232 has a diameter d' that is larger than diameter d and a second transverse cross-sectional area that is larger than the first transverse cross-sectional area. It is to be appreciated that sheath body 230 is configured to radially expand locally along the longitudinal length as necessitated by the passage of the different portions of the inserted interventional device until the interventional device passes through lumen 232. After the interventional device exits lumen 232, sheath body 230 is configured to automatically relax (i.e., the overlapping portions of sheath body 230 move toward each other and the amount of overlap increases).

It is to be appreciated that the ability for sheath body 230 to relax from its expanded state after an interventional device is withdrawn from lumen 232 is determined at least partly based on the material properties and shape/dimensional characteristics of patterned structure 250. Moreover, this ability may also be provided by the material properties and shape/dimensional characteristics of cover 260 and seal 270. For example, the elastic properties of seal 270 and the dimensions such as the inner diameters and wall thicknesses of cover 260 and seal 270 contribute to the ability for sheath body 230 to relax from its expanded state.

It is also to be appreciated that the design and material selection of sheath body 230 is configured such that, after the interventional device is removed, sheath body 230 automatically returns to its unexpanded state, where the cross-sectional area of the sheath body 230 is substantially similar to the original cross-sectional area of the sheath body 230 in the unexpanded state. In this context, "substantially similar" means sheath body 230 returns to a state that has a diameter and transverse cross-sectional area that are within 25% of the respective values of diameter d and first transverse cross-sectional area, respectively, that sheath body 230 had in the original unexpanded state.

Table 1 below includes exemplary ranges of the dimensions (wall thicknesses and widths) of the components or layers of sheath body 230. Table 1 also include an exemplary dimension that may be used in one aspect of sheath body 230 for each layer within the corresponding range of the component.

TABLE 1

| Sheath Component | Component No. | Exemplary Wall Thickness Range | Exemplary Thickness | Exemplary Width |
|---|---|---|---|---|
| Liner | 240 | .0005"-.005" | .002" | N/A |
| Coil/Wire of Patterned Structure | 250 | .001-.005" | .003" | .01" |
| Cover | 260 | .003-.02" | .006" (sheath body) .012" (proximal end) | N/A |
| Seal | 270 | .001-.005" | .003" | N/A |

Figure 12:
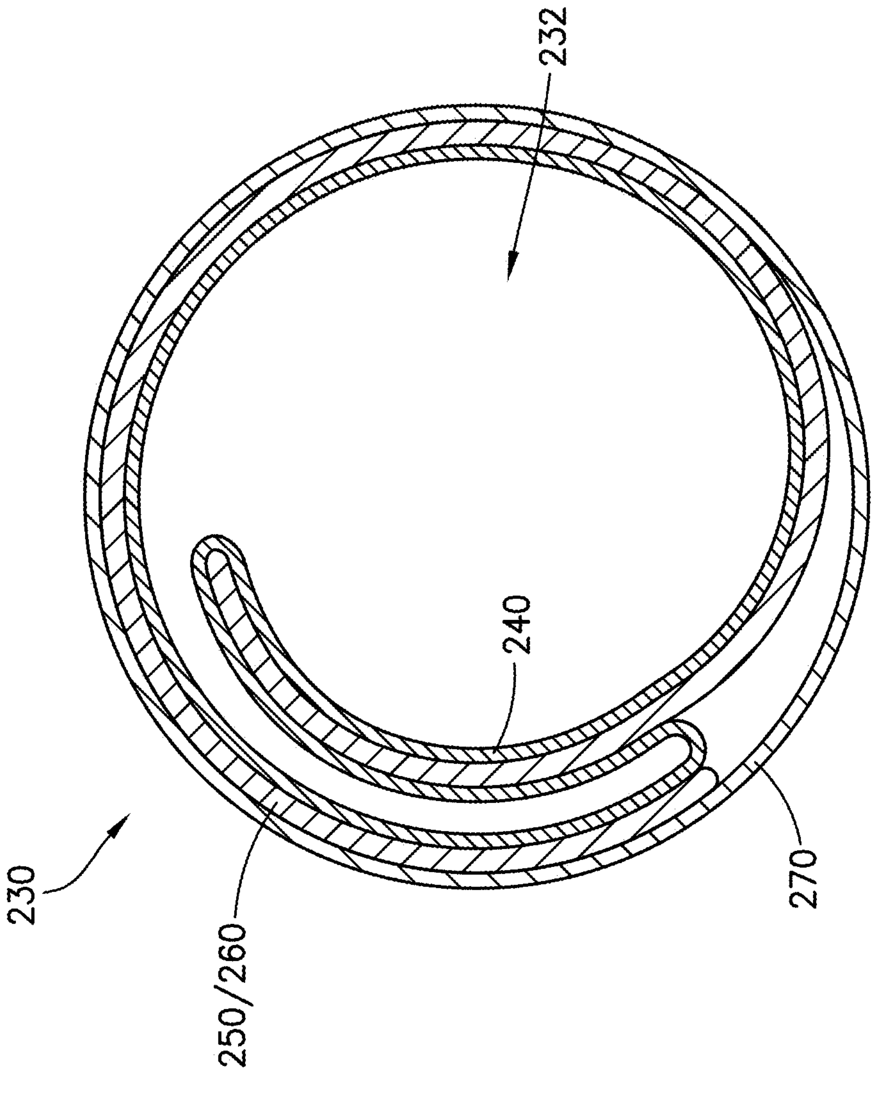
FIG. 12 is a transverse cross-sectional view of a sheath body in accordance with another aspect of the present technology.

In one aspect, the liner 240 is not slitted (i.e., slit 234 does not extend through liner 240) and in a transverse cross-section of the liner 240, the liner 240 is continuous and does not include any breaks in a circumference of the liner (i.e., the circumference of the liner 240 forms a closed loop about longitudinal axis 201 in the transverse cross-section). In this aspect, a portion of the liner 240 that extends longitudinally along sheath body 230 is folded. For example, this aspect is illustrated in FIG. 12 in accordance with the present technology. As shown in FIG. 12, in this aspect, liner 240 is not slit and a portion of liner 240 is folded on itself. It is to be appreciated that in FIG. 12, structure 250 and cover 260 are illustrated as a single layer for simplicity only. The folded portion of the liner 240 and the slitted and overlapping arrangement of patterned structure 250 and cover 260 together enable sheath body 230 to be radially expandable about longitudinal axis 201. In this aspect, since liner 240 does not have a slit and is continuous, liner 240 is configured to seal lumen 232. With liner 240 providing a seal for lumen 232, in this aspect, sheath body 230 may not include the seal or cover 270. Alternatively, as shown in FIG. 12, the sheath body 230 may include seal 270.

In any of these aspects, the sheath assembly 200 including sheath body 230 may be provided to a physician with a dilator that is inserted into the lumen 232 of sheath body 230 to facilitate smooth insertion of sheath body 230 into the vasculature of a patient. For example, after receiving sheath assembly 200 and the dilator, the physician may flush the sheath body 230 through a sidearm, such as sidearm 160, of the sheath assembly. Then, the dilator is inserted through the proximal end of hub 110 (and the valve contained therein) and through lumen 232 of sheath body 230. It is to be appreciated that the dilator has a smaller diameter or transverse cross-sectional area than sheath body 230 and thus sheath body 230 does not radially expand (and remains in the unexpanded state) when the dilater is inserted into lumen 232. The sheath body 230 is then delivered into the vasculature of the patient and the dilator is then withdrawn from lumen 232. With sheath body 230 deployed within the patient, an interventional device, such as an intracardiac heart pump, is inserted through lumen 232. In the event that portions of the interventional device include a larger diameter or transverse cross-sectional area than lumen 232 when sheath body 230 is in the unexpanded state, the first longitudinal edge 282 and the second longitudinal edge 284 of the sheath body may advance in opposing radial directions. In other words, the first longitudinal edge 282 and the second longitudinal edge 284 of the sheath body may move closer together and the overlapping portions of sheath body 230 will move away from each other. As a result, the diameter or transverse cross-sectional area of lumen 232 will increase locally as needed such that sheath body 230 is (locally) in an expanded state to allow passage of the inserted interventional device. After the interventional device is removed from lumen 232, sheath body 230 relaxes (i.e., the overlapping portions of sheath body 230 move toward each other) and the diameter or transverse cross-sectional area of lumen 232 decreases to a diameter that is substantially similar to the diameter d and the first transverse cross-sectional area of lumen 232 in the unexpanded state.

In one aspect, seal 270 may be fully bonded (e.g., fully thermoformed or dispensed dipped) over or on the exterior of cover 260 such that the bond extends around the entire circumference of the exterior of cover 260. For illustrative purposes, such a full bonding of seal 270 to cover 260 is shown in FIG. 6A. However, in other aspects, seal 270 may be selectively bonded only to a portion of the circumference of cover 260 that is on the diametrically opposite side of the overlapping portion of sheath body 230 (i.e., opposite of fold 280) to reduce strain on the sheath body 230 during radial expansion and allow for easier interventional device delivery through sheath body 230. In this regard, by not bonding seal 270 to the exterior of cover 260 along the overlapping portion of sheath body 230, the overlapping edges of sheath body 230 may separate and/or come together more easily and with less strain to enable easier radial expansion/contraction of sheath body 230.

Figure 6B:
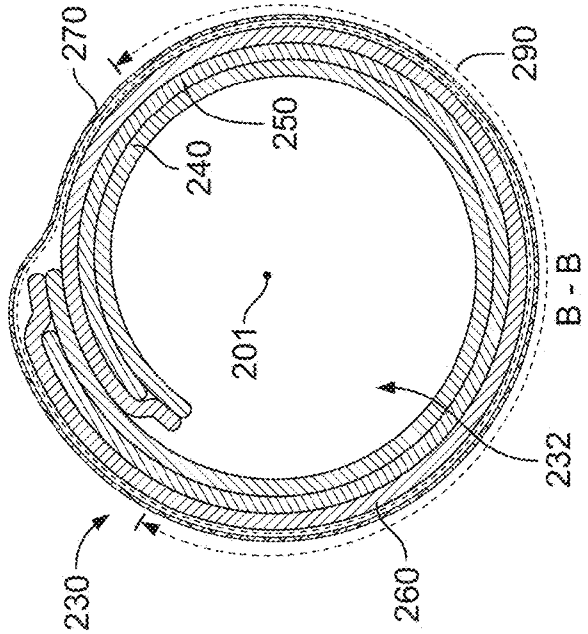
FIGS. 6A-6C are transverse cross-sectional views of the sheath body of the sheath assembly of FIG. 2 along line B-B.
Figure 6C:
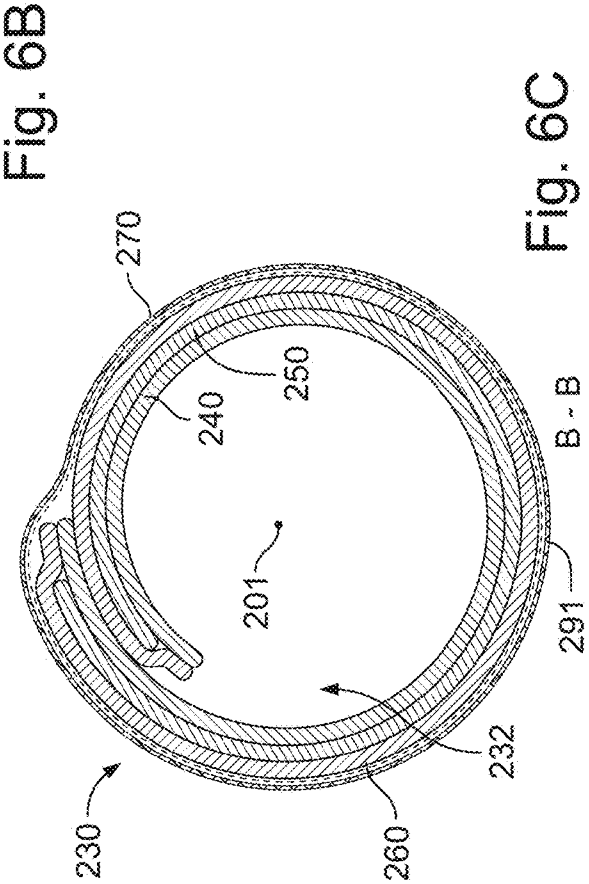
Figure 6A:
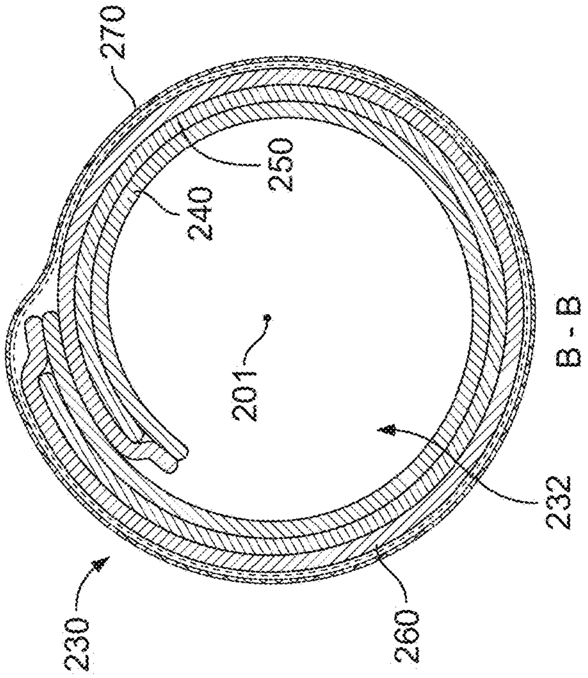

For example, in FIG. 6B, seal 270 is selectively bonded (e.g., selectively thermoformed) to a predetermined portion 290 (e.g., 70%) of the outer circumference of cover 260 that is opposite to the overlapping portion of sheath body 230. It is to be appreciated that the predetermined portion 290 of the outer circumference of cover 260 that is bonded to seal 270 may comprise any percentage or proportion of the outer circumference of cover 260, e.g., 5%, 10%, 40%, 70%, 90% etc., and may be selected to tune the strain, elasticity, and/or force required to cause sheath body 230 to radially expand. In one aspect, as shown in FIG. 6C, seal 270 may be bonded or tacked (e.g., using UV-cured glue, heat, cyanoacrylate (CA) adhesive, etc.) only to a small region or point 291 of the outer circumference of cover 260 (e.g., 0.1-5% of the outer circumference of cover 260) approximately opposite to the overlapping portion of sheath body 230.

Figure 7:
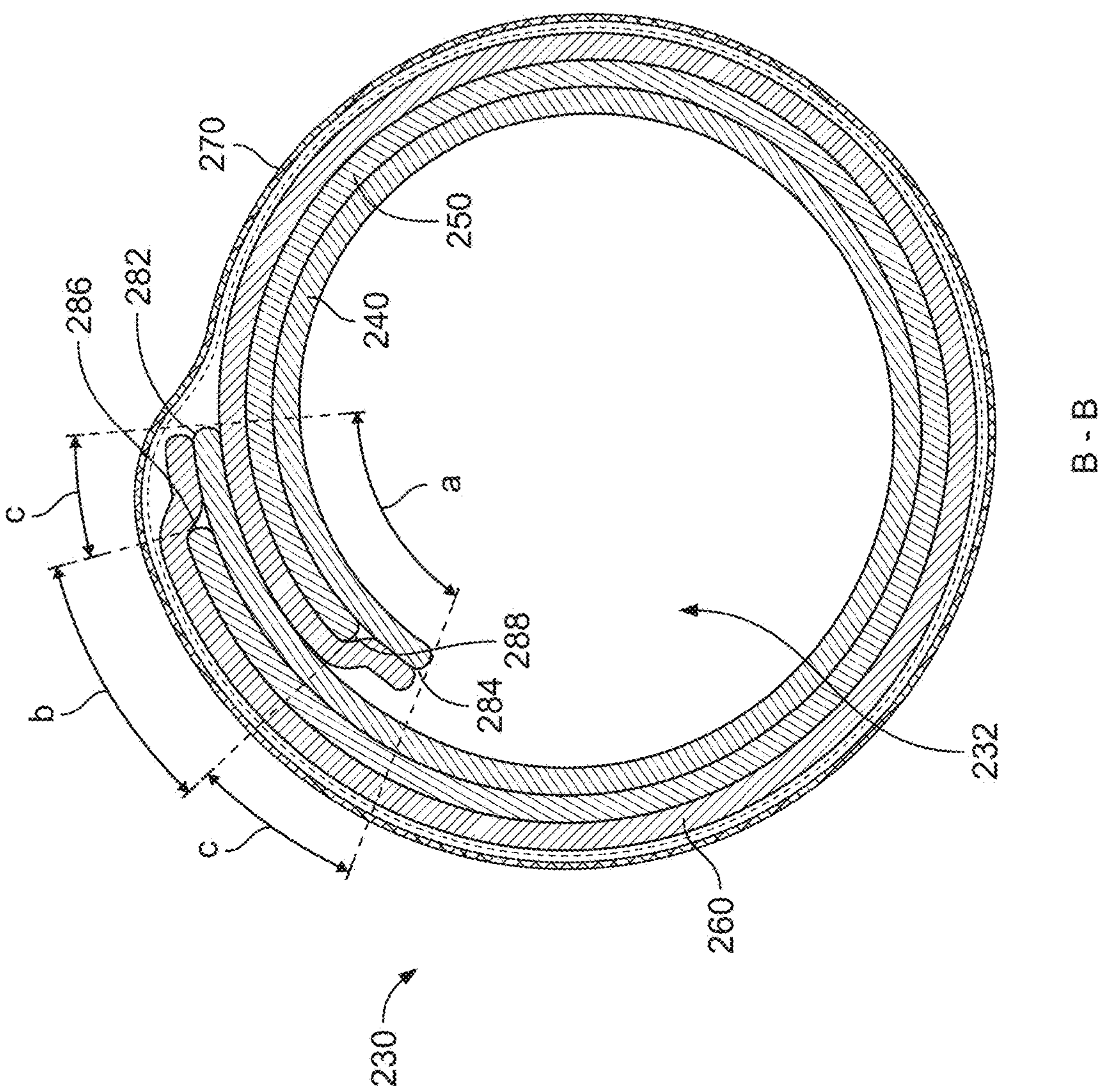
FIG. 7 is a transverse cross-sectional view of the sheath body of the sheath assembly of FIG. 2 along line B-B.

It is to be appreciated that, in some aspects, different layers (240, 250, 260) of sheath body 230 may have different amounts of overlap. For example, as shown in FIG. 7, in one aspect, liner 240 and cover 260 each have the same circumference (measured from longitudinal edge 282 to longitudinal edge 284 and patterned structure 250 has a circumference that is less than the circumference of liner 240 and cover 260. When sheath body 230 is in the unexpanded state, as shown in FIG. 7, the overlapping portions of liner 240 and cover 260 may overlap by a predetermined amount a. In one aspect, sheath body 230 is configured to receive an intracardiac heart pump through lumen 232. In this aspect, overlap a is approximately (e.g., +/−25%) 6.3 mm when sheath body 230 is in the unexpanded state. The overlap a may decrease to approximately (e.g., +/−25%) 1.3 mm when the largest portion of an intracardiac blood pump is inserted through lumen 232 and the sheath body 230 is in the expanded state. Thus, the circumferential expansion of sheath body 230 in this aspect is approximately (e.g., +/−25%) 5 mm. The diameter of lumen 232 in the unexpanded state is approximately (e.g., +/−25%) 3.5 mm and the diameter of lumen 232 in the expanded state is approximately (e.g., +/−25%) 5.1 mm in this aspect.

As shown in FIG. 7, in this aspect, the patterned structure 250 has a smaller circumference than the circumference of liner 240 and cover 260. Thus, the longitudinal edges 282, 284 of liner 240 and cover 260 each overhang or extend circumferentially beyond each of longitudinal edges 286, 288, respectively, of patterned structure 250 by a predetermined amount c. In one aspect, the predetermined amount c is approximately (e.g., +/−25%) 1 mm. When sheath body 230 is in the unexpanded state, the overlapping portions of patterned structure 250 may overlap by a predetermined amount b that is less than the overlap a between the overlapping portions of liner 240 and cover 260. In one aspect, the overlap of the coil may be at least 1 mm.

It is to be appreciated that, by selecting the predetermined overlap b to be less than the predetermined overlap a between the overlapping portions of liner 240 and 260, the possibility that the ends of the patterned structure 250 protruding or extending through the slit edges of sheath body 230 during normal use is reduced. Additionally, when liner 240 is not slit (as described above), by selecting the overlap a to be larger than overlap b, the amount of folding or overlapping of the folded portion of liner 240 is increased, which enables a larger range of radial expansion and contraction for sheath body 230.

It is to be appreciated that the predetermined overlap b in patterned structure 250 when sheath body 230 is in the unexpanded state enables sheath body 230 to resist kinking while still also enabling sheath body 230 to be flexible enough to maneuver through the vasculature of the patient when in use during a procedure. In addition, the predetermined overlap b further may be selected such that there is an overlap even when the sheath body 230 is in the expanded state. Thus, the overlap b enables the sheath body 230 to relax from the expanded state to the collapsed state. In this regard, if there is no overlap between the edges of patterned structure 250, the edges of the slit may catch on each other and prevent the sheath body from returning to the collapsed state.

Figure 8A:
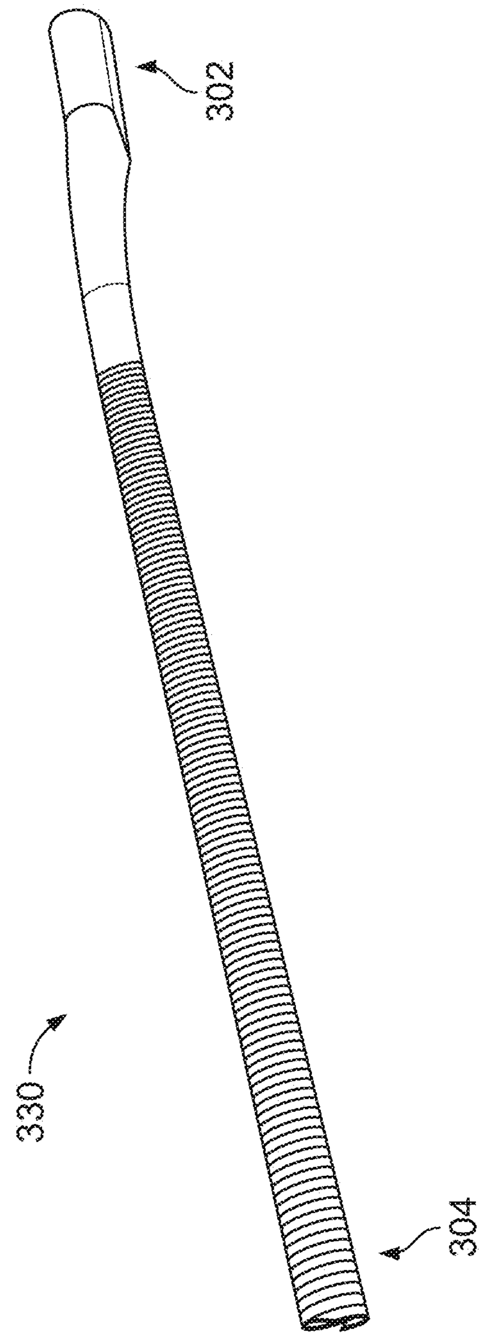
FIG. 8A is a perspective view of a radially expandable sheath body in accordance with an aspect of the present technology.
Figure 8B:
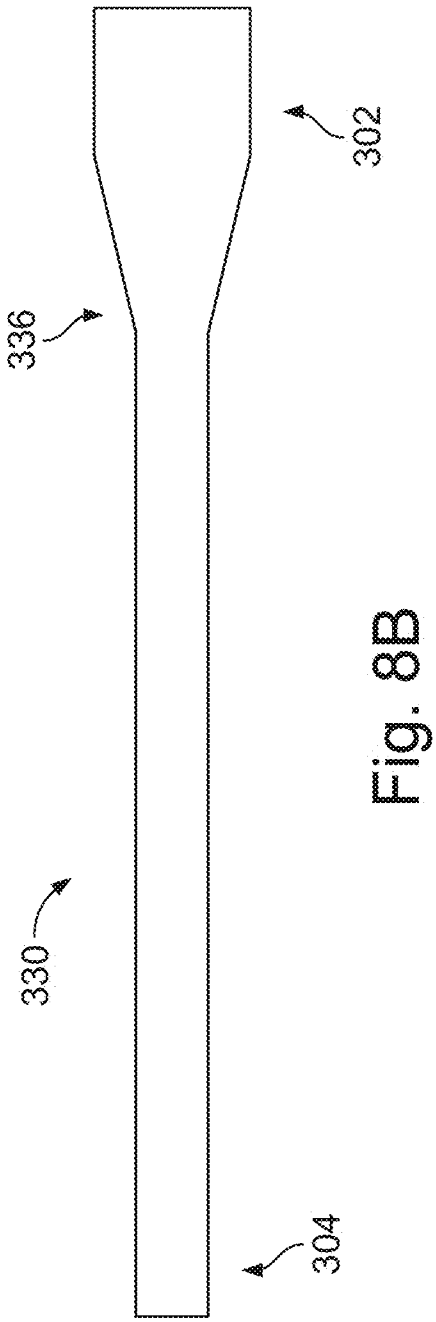
FIG. 8B is a side view of the radially expandable sheath body of FIG. 8A.

In one aspect, as shown in FIG. 5A, sheath body 230, when in a relaxed state and unexpanded state, may include a constant diameter or transverse cross-sectional area from the proximal end 202 to the distal end 204. In another aspect, sheath body 230 may be configured with a flared proximal end 202 when sheath body 230 is in a relaxed state and unexpanded state. For example, referring to FIGS. 8A and 8B, a radially expandable sheath body 330 is shown in accordance with an aspect of the present technology. Sheath body 330 is configured with the same features (e.g., the multilayered overlapping sheath body arrangement described above) as sheath body 230. However, in contrast to sheath body 230, sheath body 330 includes a proximal portion that has a larger diameter and larger transverse cross-sectional area than the central and distal portions of sheath body 330. In this regard, the proximal portion of sheath body 330 may comprise a tapered portion 336 that transitions the diameter of sheath body 330 from a first diameter to a second diameter, where the first diameter is smaller than the second diameter. The first diameter is the diameter of the central and distal portions of sheath body 330 and the second diameter is the diameter of the proximal end 302 of sheath body 330. The proximal end 302 may be bonded, overmolded, or attached mechanically to hub 110.

Figure 9:
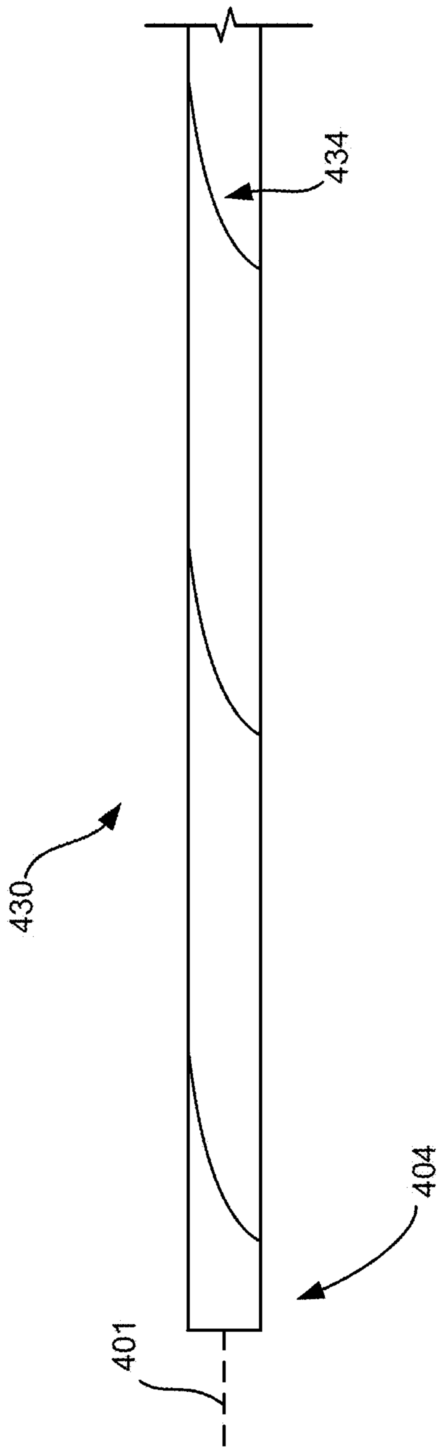
FIG. 9 is a side view of a radially expandable sheath body in accordance with another aspect of the present technology.

Referring again to FIG. 5A, in one aspect, slit 234 extends linearly in parallel to axis 201 along sheath body 230. In another aspect, sheath body 230 may have a non-linear slit from the distal end 204 toward the proximal end 202 as illustrated in FIG. 9. Referring to FIG. 9, a sheath body 430 including a non-linearly extending slit 434 is shown in accordance with an aspect of the present technology. It is to be appreciated that sheath body 430 is shown in FIG. 9 without a sealing layer (such as seal 270). It is also to be appreciated that sheath body 430 includes any of the features of sheath bodies 230, 330 described above. However, the slit 434 of sheath body 430 is rotated through the longitudinal length of shaft body 430 such that the slit 434 extends from distal end 404 of sheath body 430 along a coiled or helix-shaped path about longitudinal axis 401 toward a proximal end of sheath body 430. The non-linearly extending slit 434 shown in FIG. 9 may increase the kink resistance of sheath body 430. It is to be appreciated that the non-linearly extending slit 434 may be selected as desired to tune the kinking and/or other operational characteristics of sheath body 430. For example, the pitch may be selected such that non-linearly extending slit 434 has a predetermined number of turns or a fraction of a turn (or turns) through the longitudinal length of shaft body 430 in various aspects of the present technology. For example, the pitch may be selected such that the slit 434 may have multiple turns (i.e., 2 or more) as shown in FIG. 9. Alternatively, the pitch may be selected such that slit 434 may have a single turn through the length of sheath body 430. Alternatively, the pitch may be selected such that slit 434 may be rotated a fraction of a turn (e.g., 0.1, 0.5, 0.8, etc.) or a fraction of multiple turns (e.g., 1.2, 1.5, 2.3, etc.) through the length of sheath body 430.

Figure 10:
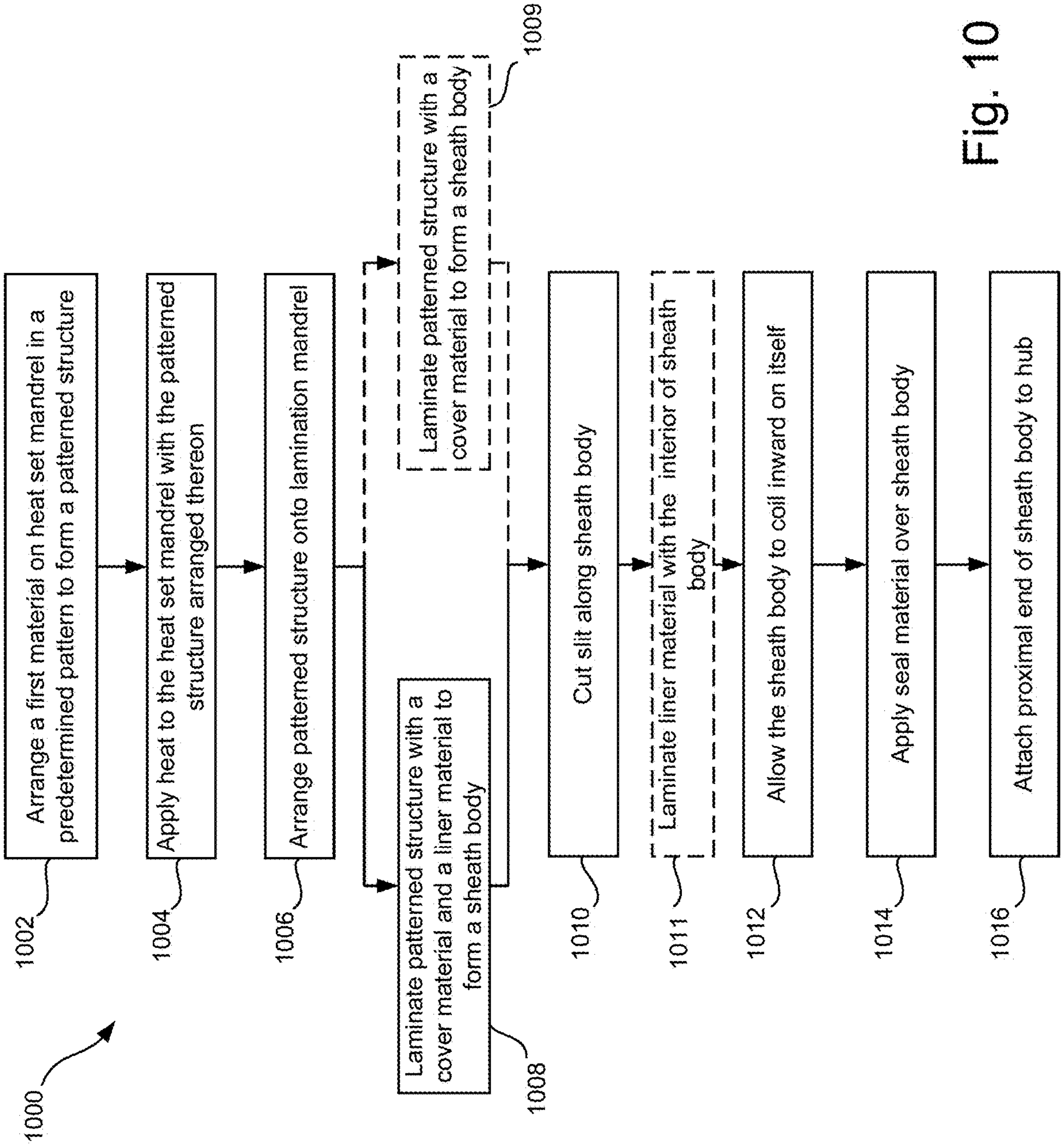
FIG. 10 illustrates a method of manufacturing a radially expandable sheath assembly in accordance with an aspect of the present technology.

Referring to FIG. 10, a method 1000 for manufacturing a reversibly radially expandable sheath body, such as sheath body 230, 330, 430, for use in a sheath assembly, such as sheath assembly 100, 200 is shown in accordance with an aspect of the present technology. In step 1002, a first material is arranged on a tubular heat set mandrel in a predetermined pattern to form patterned structure 250 over the heat set mandrel. For example, as described above in reference to patterned structure 250, the first material may be a metal wire, such as Nitinol or stainless steel wire. Moreover, the patterned structure 250 may be a coil or a braid. In the case of a coil pattern, the metal wire is coiled tightly around the heat set mandrel. The heat set mandrel has a first diameter. For example, in one aspect the first diameter is 2.8 mm. In another aspect, the first diameter is 3.3 mm. However, it is to be appreciated that other values for the first diameter may be used. In one aspect, the heat set mandrel may be tapered from one diameter (e.g., 2.8 mm) to a larger outer diameter (e.g., 5 mm) to aid in preventing delamination on the inner diameter of sheath body 230 after laminating the liner.

In step 1004, heat is applied to the heat set mandrel with the patterned structure 250 arranged thereon to set the shape of the patterned structure 250. For example, the heat set mandrel with the patterned structure 250 may be placed in an oven at a predetermined temperature, such as 500 degrees Celsius, for a predetermined time, such as 9 minutes. It is to be appreciated that the predetermined temperature and time are exemplary and other temperatures and/or times may be used to alter the properties of the patterned structure 250. For example, in one aspect, the predetermined temperature is in a range of 450-550° C. and the predetermined time is in a range of 5-20 minutes.

In step 1006, the patterned structure 250 is arranged onto a lamination mandrel having a second diameter. In one aspect, the second diameter may be selected based on the largest diameter of the interventional device to be inserted into the lumen 232 of the sheath body 230 when formed and based on the necessary overlap needed in the sheath body 230 to allow the sheath body to return to the collapsed state easily from the expanded state. For example, in one aspect, the interventional device is an intracardiac heart pump and the second diameter is 5.5 mm, which may enable insertion of the pump section of the intracardiac heart pump (i.e., the portion of the pump with the largest diameter). If the pattern for the patterned structure 250 is a coil, the patterned structure 250 is recoiled onto the lamination mandrel with a predetermined pitch. In one aspect, the pitch is 30 wraps per inch, however other pitches may be selected.

Figure 11:
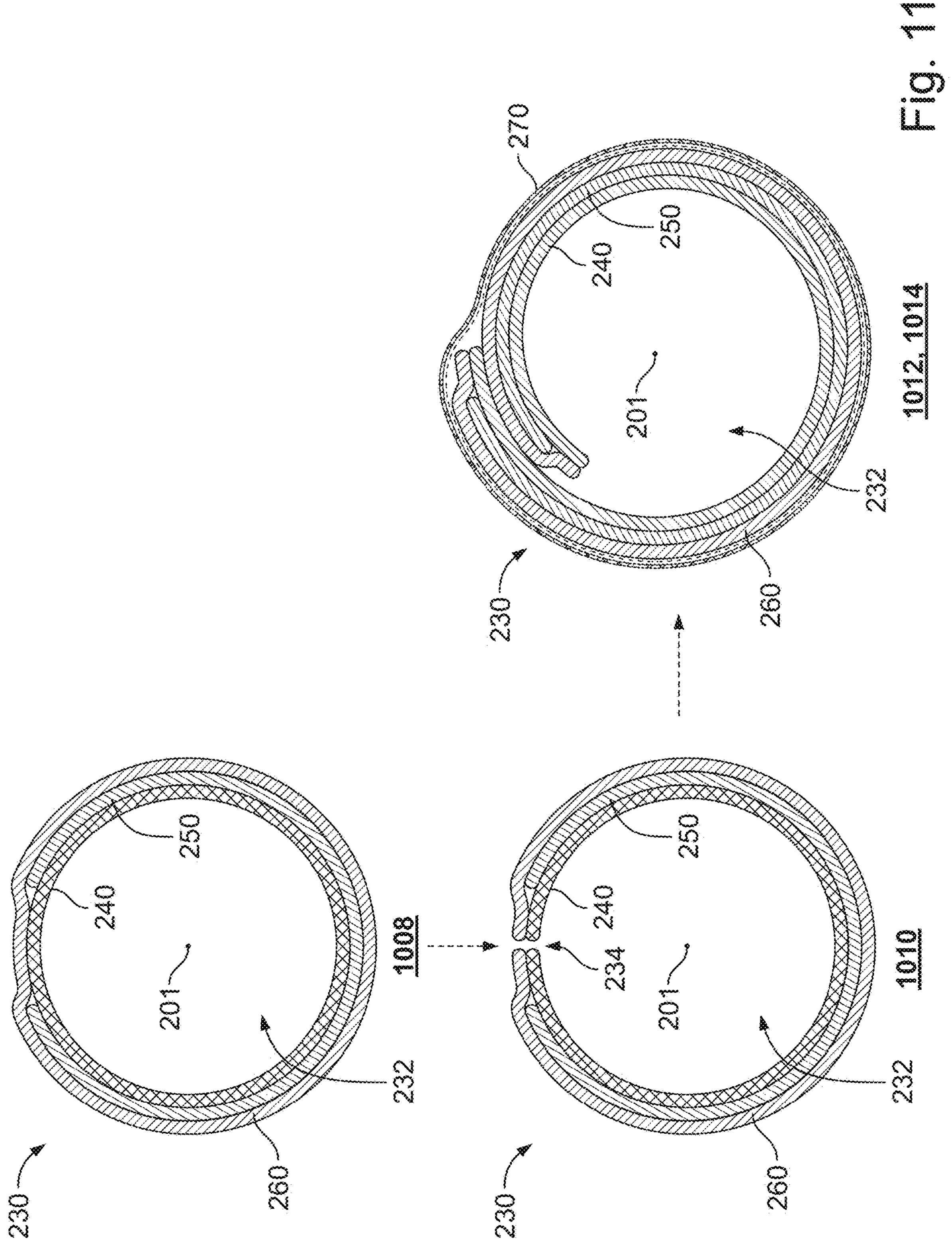
FIG. 11 includes illustrations of transverse cross-sectional views of the sheath body of the sheath assembly of FIG. 2 along line B-B to illustrate steps in the method of FIG. 10 in accordance with aspects of the present technology.

In step 1008, the patterned structure 250 is laminated with a cover material for cover 260 and a liner material for liner 240, such that the patterned structure 250 is disposed between the cover 260 and liner 240 to form a multilayered tubular sheath body, such as sheath body 230. The result of step 1008 is illustrated in FIG. 11, where a transverse cross-sectional view of sheath body 230 after step 1008 is performed is shown. As shown in FIG. 11, cover 260, patterned structure 250, and liner 240, are formed such that cover 260, patterned structure 250, and liner 240 are coaxially arranged, with cover 260 forming the outermost layer and liner 240 forming the innermost layer of sheath body 230. It is to be appreciated that in step 1008, the cover material may be extruded onto the liner material. Moreover, the patterned structure 250 may be embedded in the cover 260, as described above and shown in FIG. 3. Additionally, the cover material may be a polymer, such as, TPU or a polyether block amid, and the liner material may be a lubricious material such as PTFE.

In step 1010, a slit 234 is cut longitudinally along the sheath body 230 from the distal end 204 toward the proximal end 202. It is to be appreciated that the slit 234 may terminate a predetermined distance before the proximal end 202. In one aspect, the predetermined distance is 3.4 cm. In one aspect, the slit may terminate at or just before a tapered proximal portion (e.g., as shown in FIG. 6) of the sheath body 230. The result of step 1010 is illustrated in FIG. 11, where a transverse cross-sectional view of sheath body 230 after step 1010 is performed is shown.

Figure 13:
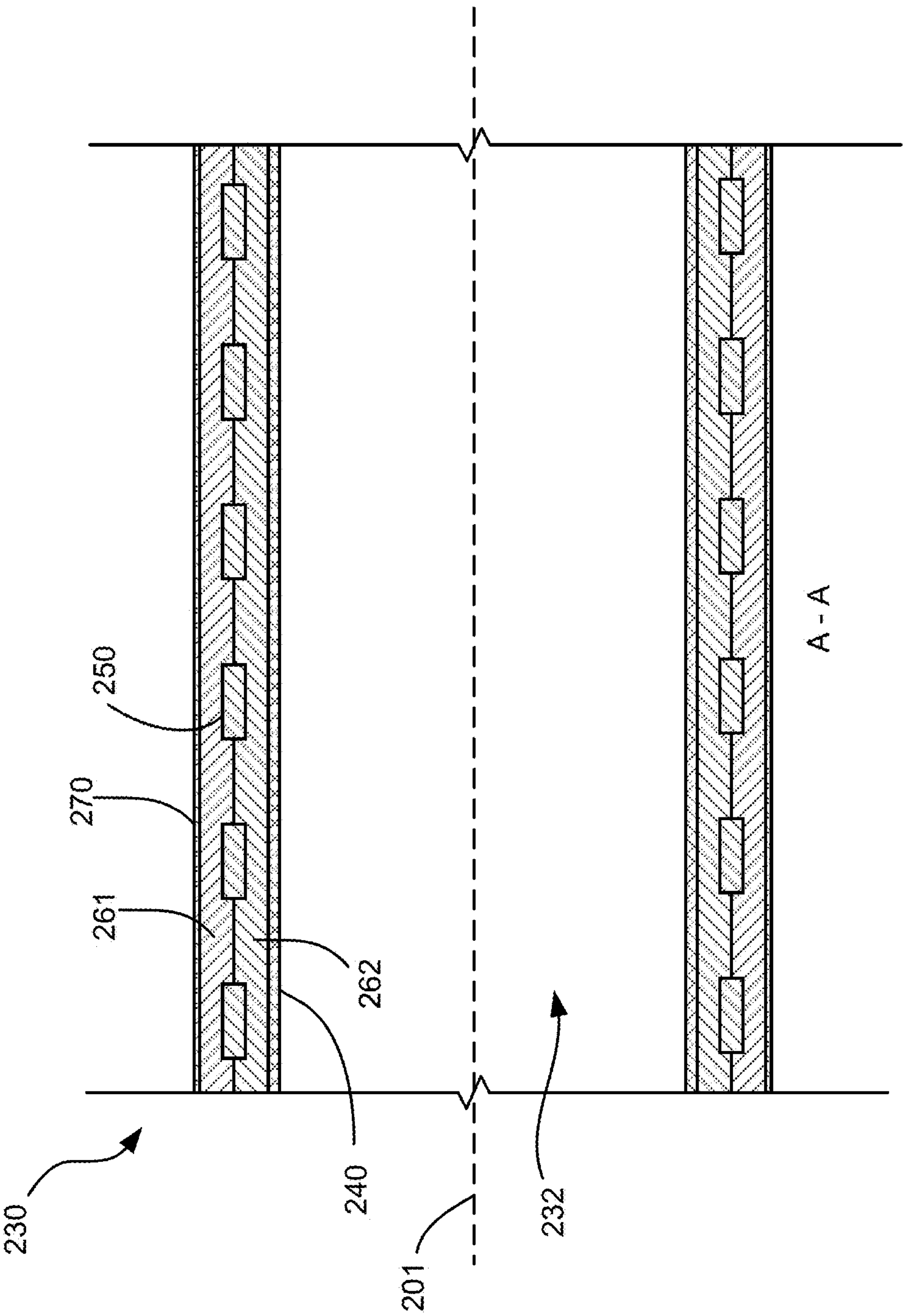
FIG. 13 is a longitudinal cross-sectional view of a sheath body in accordance with another aspect of the present technology.

In another aspect of method 1000, where liner 240 is not slit (as described above and shown in FIG. 12), step 1008 is replaced by step 1009, as shown in FIG. 10. In step 1009, the patterned structure is laminated to the cover material. In one aspect, step 1009 may be performed in two sub-steps. In a first sub-step, a first layer of cover material is laminated onto a mandrel and, in a second sub-step, the patterned structure 250 is added and a second layer of the cover material is laminated over the patterned structure 250 on an opposite side to the first layer of cover material. Referring to FIG. 13, a cross-sectional view of sheath body 230 with the features of this aspect is shown in accordance with the present technology. As shown, in this aspect, the cover comprises first and second layers 261, 262 with patterned structure 250 embedded between cover layers 261, 262. Thus, patterned structure 250 is encapsulated on all sides by layers 261, 262 of the cover material (which together form cover layer 260).

Then, in step 1010, the patterned structure and the cover material are slit along the sheath body and, in step 1011, the liner is laminated to the interior of the sheath body. In one aspect, for step 1011, a different size mandrel or materials for masking can be used to laminate the liner material to the interior of the sheath body to prevent any unwanted forming of the cover material when it is reheated. For example, in this aspect, after the patterned structure 250 and cover material are slit, when the patterned structure 250 and cover material are laminated onto the interior liner layer, the lamination occurs on a mandrel with a smaller diameter than the mandrel used in step 1009. The purpose of the smaller diameter mandrel is to allow the slit sheath body to be formed into the desired shape in step 1011. Due to this smaller mandrel, the cover material may form or bond to itself during this lamination step thereby preventing the wrapped sheath from expanding when complete. To prevent this from occurring, the dimensions of the interior liner layer and the mandrel are selected to allow for an overlap in the interior liner layer to block the cover layer from coming into contact with itself when the sheath body is wrapped. Alternatively, a masking technique may be used to prevent such contact.

In either aspect of method 1000, in step 1012, sheath body 230 is allowed to coil inward on itself such that a first portion of sheath body 230 extending along the slit 234 and a second portion of sheath body 230 extending along the slit 234 overlap to form a longitudinal fold. It is to be appreciated that if liner 240 is not slit (i.e., step 1009 is performed), at step 1012, a portion of the liner 240 extending along the longitudinal length of the sheath body is folded to overlap. In either case, after the sheath body 230 is slit, the patterned structure is configured to apply a coiling force to the sheath body 230 to cause the sheath body 230 to coil inward on itself. In step 1014, a sealing material (e.g., an elastomer) is applied over cover 260 to form a seal 270 configured to seal the slit 234 to prevent fluid, such as blood, from escaping the lumen 232 via the slit 234 when sheath body 230 is inserted into the patient vasculature. The result of steps 1012 and 1014 (with the liner 240 is slit) is shown in FIG. 11, where a transverse cross-sectional view of sheath body 230 that results after steps 1012 and 1014 is shown. In one aspect, step 1012 includes shrink wrapping the seal material over cover 260. In step 1016, the proximal end 202 of sheath body 230 is attached to a sheath hub, such as hub 110 to form an expandable sheath assembly, such as sheath assembly 200.

In another aspect, method 1000 may also include an additional step prior to applying the seal material (step 1014) and attaching the hub (step 1016) where the sheath body 230 is laminated again on a tapered mandrel and heated again to form the proximal end.

In this step, the cover material is attached to the sheath body. It can be attached at the proximal and distal ends of the sheath body or down the full length of the sheath. It can be attached with the sheath body in its coiled form or by expanding the sheath on a larger mandrel. Alternatively, an additional step can be performed on a larger diameter mandrel to heat up the sheath body 230 to allow the cover to encapsulate the patterned structure 250.

The coiled design of sheath body 230, 330, 430 and method 1000 of manufacturing the same provide many advantages over existing sheath assemblies and reduces or eliminates many of the disadvantages with existing sheath assemblies discussed above. For example, the seal 270 seals the slit 234 along sheath body 230 and is configured to prevent bleeding/thrombus formation during prolonged use of the sheath assembly 200 within a patient. Moreover, sheath body 230 leverages the patterned structure 250 to increase the amount of kink resistance relative to existing sheath assembly designs and provide excellent column strength. The increased kink resistance aids in a safer procedure. The folded arrangement and use of patterned structure 250 enables the sheath body 230 to radially expand to an expanded state and also to automatically recoil to a state that is substantially similar to the original unexpanded state without requiring an actuation mechanism manually operated by the user. Furthermore, the folded arrangement enables sheath body 230 have a reduced diameter relative to fixed diameter sheaths bodies. Still further, the proposed design of sheath body 230 is easily manufacturable.

In one aspect of the present technology, an expandable sheath is provided comprising an elongate sheath body having a proximal end, a distal end, and a lumen extending from the proximal end to the distal end. The elongate sheath body comprises a first layer, a second layer, and a third layer. The first layer is a liner defining the lumen. The second layer is disposed over the first layer and the second layer is a patterned structure. The third layer disposed over the second layer. The elongate sheath body includes a slit through the second layer and the third layer, wherein the slit extends along at least a portion of the elongate sheath body. The first portion of the elongate sheath body overlaps a second portion of the elongate sheath body along the slit to form a fold.

In some aspects, the elongate sheath body is configured to radially expand from an unexpanded state to an expanded state to allow passage of a portion of a medical device through the lumen and the portion of the medical device has a transverse cross-sectional area larger than a transverse cross-sectional area of the lumen when the elongate sheath body is in the unexpanded state.

In some aspects, the medical device is an intracardiac heart pump.

In some aspects, when the elongate sheath body is radially expanded, the overlap between the first portion of the elongate sheath body and the second portion of the elongate sheath body is decreased and the transverse cross-sectional area of the lumen thereby increases.

In some aspects, the elongate sheath body is configured to relax when the portion of the medical device is removed from the lumen such that the transverse cross-sectional area of the lumen is decreased and the elongate sheath body substantially returns to the cross-sectional area in the unexpanded state.

In some aspects, the first layer is made of polytetrafluoroethylene (PTFE) or an elastomer.

In some aspects, the first layer includes a lubricious coating on an interior surface of the first layer.

In some aspects, the first layer includes a hydrophilic coating on an interior surface of the first layer.

In some aspects, the slit of the elongate sheath body is further through the first layer.

In some aspects, the first layer includes a folded portion that extends along at least a portion of the elongated sheath.

In some aspects, in a transverse cross-section of the first layer, the first layer is continuous and does not include any breaks in a circumference of the first layer.

In some aspects, the second layer is made of metal.

In some aspects, the metal is stainless steel or nitinol.

In some aspects, the patterned structure is a coil.

In some aspects, the patterned structure is embedded within the third layer.

In some aspects, the third layer is made of thermoplastic.

In some aspects, the third layer is made of thermoplastic polyurethane (TPU) or a polyether block amid.

In some aspects, the elongate sheath body is tubular.

In some aspects, the elongate sheath body further comprises a fourth layer disposed over the third layer, the fourth layer configured to seal the fold in the elongate sheath body.

In some aspects, the fourth layer is made of an elastomer.

In some aspects, the fourth layer is made of TPU or silicone.

In some aspects, the expandable sheath further comprises a hub, wherein the proximal end of the elongate sheath body is coupled to the hub.

From the foregoing and with reference to the various figure drawings, those skilled in the art will appreciate that certain modifications can also be made to the present disclosure without departing from the scope of the same. While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

The invention claimed is:

1. An expandable sheath comprising:

an elongate sheath body having a proximal end, a distal end, and a lumen extending from the proximal end to the distal end, wherein the elongate sheath body is radially expandable from an unexpanded state to an expanded state and radially contractable from the expanded state, wherein the elongate sheath body comprises:

a first layer, wherein the first layer is a liner defining the lumen;

a second layer disposed over the first layer, wherein the second layer is a patterned structure;

a third layer disposed over the second layer; and a fourth layer disposed over the third layer, wherein the elongate sheath body includes a slit through the second layer and the third layer, wherein the slit extends from the distal end toward the proximal end of the elongate sheath body, wherein, in the unexpanded state, a first portion of the elongate sheath body overlaps a second portion of the elongate sheath body along the slit to form a fold, and wherein the fourth layer has elastic properties and is configured to seal the slit while permitting the elongate sheath body to radially expand and radially contract.

2. The expandable sheath of claim 1, wherein the elongate sheath body is configured to radially expand from the unexpanded state to the expanded state to allow passage of a portion of a medical device through the lumen, the portion of the medical device having a transverse cross-sectional area that is larger than a transverse cross-sectional area of the lumen when the elongate sheath body is in the unexpanded state.

3. The expandable sheath of claim 2, wherein the medical device is an intracardiac heart pump.

4. The expandable sheath of claim 2, wherein, when the elongate sheath body is radially expanded, the overlap between the first portion of the elongate sheath body and the second portion of the elongate sheath body is decreased and the transverse cross-sectional area of the lumen thereby increases.

5. The expandable sheath of claim 2, wherein the elongate sheath body is configured to radially contract when the portion of the medical device is removed from the lumen such that the transverse cross-sectional area of the lumen is decreased.

6. The expandable sheath of claim 1, wherein the first layer is made of polytetrafluoroethylene (PTFE) or an elastomer.

7. The expandable sheath of claim 1, wherein the first layer includes a lubricious coating on an interior surface of the first layer.

8. The expandable sheath of claim 1, wherein the first layer includes a hydrophilic coating on an interior surface of the first layer.

9. The expandable sheath of claim 1, wherein the slit of the elongate sheath body is further through the first layer.

10. The expandable sheath of claim 1, wherein the first layer includes a folded portion that extends along the slit, wherein, in a transverse cross-section of the first layer, the first layer is continuous and does not include any breaks in a circumference of the first layer.

11. The expandable sheath of claim 1, wherein the second layer is made of metal.

12. The expandable sheath of claim 11, wherein the metal is stainless steel or nitinol.

13. The expandable sheath of claim 1, wherein the patterned structure is a coil.

14. The expandable sheath of claim 1, wherein the patterned structure is embedded within the third layer.

15. The expandable sheath of claim 1, wherein the third layer is made of thermoplastic.

16. The expandable sheath of claim 1, wherein the third layer is made of thermoplastic polyurethane (TPU) or a polyether block amid.

17. The expandable sheath of claim 1, wherein the elongate sheath body is tubular.

18. The expandable sheath of claim 1, wherein the fourth layer is configured to prevent fluid from leaking out of the lumen through the slit.

19. The expandable sheath of claim 18, wherein the fourth layer is made of an elastomer, a thermoplastic polyurethane (TPU), or silicone.

20. The expandable sheath of claim 1, further comprising a hub, wherein the proximal end of the elongate sheath body is coupled to the hub.

21. The expandable sheath of claim 1, wherein the slit extends non-linearly along the elongate sheath body.

22. The expandable sheath of claim 1, wherein the fourth layer is bonded to a first portion of an exterior of the third layer and the fourth layer is not bonded to a second portion of the exterior of the third layer, wherein the second portion of the exterior of the third layer forms a part of the fold.

* * * * *